United States Patent [19]
Wijay

[11] Patent Number: 5,741,293
[45] Date of Patent: Apr. 21, 1998

[54] LOCKING STENT

[76] Inventor: Bandula Wijay, 1903 Carriage Creek Dr., Friendswood, Tex. 77546

[21] Appl. No.: 563,375

[22] Filed: Nov. 28, 1995

[51] Int. Cl.$^6$ ............................................. A61M 29/00
[52] U.S. Cl. ........................... 606/198; 623/1; 623/12
[58] Field of Search ........................... 606/1, 191, 194, 606/195, 198, 200; 623/1, 12

[56] References Cited

U.S. PATENT DOCUMENTS

| | | |
|---|---|---|
| Re. 34,037 | 8/1992 | Inuue et al. . |
| 4,503,569 | 3/1985 | Dotter . |
| 4,580,568 | 4/1986 | Gianturco . |
| 4,732,152 | 3/1988 | Wallsten et al. . |
| 4,740,207 | 4/1988 | Kreamer . |
| 4,776,337 | 10/1988 | Palmaz . |
| 4,795,458 | 1/1989 | Regan . |
| 4,820,298 | 4/1989 | Leveen et al. . |
| 4,886,062 | 12/1989 | Wiktor . |
| 4,913,141 | 4/1990 | Hillstead . |
| 4,950,227 | 8/1990 | Savin et al. . |
| 4,964,853 | 10/1990 | Sugiyama et al. . |
| 4,969,458 | 11/1990 | Wiktor . |
| 4,990,151 | 2/1991 | Wallsten . |
| 5,100,429 | 3/1992 | Sinofsky et al. . |
| 5,108,416 | 4/1992 | Ryan et al. . |
| 5,133,732 | 7/1992 | Wiktor . |
| 5,135,536 | 8/1992 | Hillstead . |
| 5,139,480 | 8/1992 | Hickle et al. . |
| 5,158,548 | 10/1992 | Lau et al. . |
| 5,160,341 | 11/1992 | Brenneman et al. . |
| 5,163,951 | 11/1992 | Pinchuk et al. . |
| 5,163,952 | 11/1992 | Froix . |
| 5,163,958 | 11/1992 | Pinchuk . |
| 5,195,984 | 3/1993 | Schatz . |
| 5,197,978 | 3/1993 | Hess . |
| 5,213,561 | 5/1993 | Weinstein et al. . |
| 5,222,969 | 6/1993 | Gillis . |
| 5,222,971 | 6/1993 | Willard et al. . |
| 5,234,457 | 8/1993 | Anderson . |
| 5,258,042 | 11/1993 | Mehta . |
| 5,266,073 | 11/1993 | Wall . |
| 5,282,823 | 2/1994 | Schwartz et al. . |
| 5,282,824 | 2/1994 | Gianturco . |
| 5,287,861 | 2/1994 | Wilk . |
| 5,292,331 | 3/1994 | Boneau . |
| 5,304,121 | 4/1994 | Sahatjian . |
| 5,306,294 | 4/1994 | Winston et al. . |
| 5,314,472 | 5/1994 | Fontaine . |
| 5,334,201 | 8/1994 | Cowan . |
| 5,336,518 | 8/1994 | Narayanan et al. . |
| 5,342,348 | 8/1994 | Kaplan . |
| 5,344,426 | 9/1994 | Lau et al. . |
| 5,360,401 | 11/1994 | Turnland . |
| 5,368,566 | 11/1994 | Crocker . |
| 5,370,691 | 12/1994 | Samson . |
| 5,383,928 | 1/1995 | Scott et al. . |
| 5,389,106 | 2/1995 | Tower . |
| 5,391,172 | 2/1995 | Williams et al. . |
| 5,397,355 | 3/1995 | Marin et al. . |
| 5,421,955 | 6/1995 | Lau et al. . |
| 5,423,885 | 6/1995 | Williams . |
| 5,433,706 | 7/1995 | Abiuso . |

OTHER PUBLICATIONS

AngioStent Balloon Expandable Stent System, AngioDynamics Division of E–Z–EM, Inc., Sept., 1994 (brochure).

Gianturco–Roubin Flex–Stent Coronary Stents, Cook Cardiology, 1995 (brochure).

Donald S. Baim, MD, "New Stent Designs," 2 pages, dated after Aug., 1995.

*Primary Examiner*—William Lewis
*Attorney, Agent, or Firm*—Rosenblatt & Redano P.C.

[57] ABSTRACT

The invention discloses a stent which has a locking feature to prevent recoil. The stent is composed of a plurality of rings which are joined by crossties of various construction. The locking feature of each ring can be in alignment or staggered. The crossties may be straight or angled or they may have curvature to them to further promote longitudinal flexibility. The locking mechanism includes features which minimize sharp ends exposed to the vascular wall.

34 Claims, 10 Drawing Sheets

U.S. PATENT DOCUMENTS

| | | |
|---|---|---|
| 5,437,632 | 8/1995 | Engelson . |
| 5,439,444 | 8/1995 | Anderson et al. . |
| 5,439,445 | 8/1995 | Kontos . |
| 5,441,515 | 8/1995 | Khosravi et al. ............................ 623/1 |
| 5,443,500 | 8/1995 | Sigwart . |
| 5,480,423 | 1/1996 | Ravenscroft et al. . |
| 5,549,662 | 8/1996 | Fordenbacher ........................... 606/198 |
| 5,556,413 | 9/1996 | Lam ......................................... 606/198 |

LOCKING STENT

FIELD OF THE INVENTION

The field of this invention relates to vascular stents that can be delivered to a predetermined position and allowed to spring outwardly or, in the alternative, which can be expanded in place.

BACKGROUND OF THE INVENTION

Vascular stents are structures that are designed to maintain the patency of a vessel in the body. The stent provides internal support to allow the circulation to proceed therethrough. Stents can be used in the vascular system in ureters, bile ducts, esophagus, and in many other tubular structures in the human body.

Stents can be tubular or can be made from wire. Stents are typically made from a metal or polymeric substance or a metal coated with polymers which are biocompatible or contain heparin to reduce blood clotting or other tissue reactions. Many prior designs have used a coil approach where a wire is helically wound on a mandrel. Yet other designs have evolved—braided wire mesh and angulated wire forms wrapped on a spindle to form a coil.

U.S. Pat. No. 5,292,331 by Boneau and U.S. Pat. No. 5,403,341 describe such wire forms. These devices have very poor radial support to withstand the hoop strengths of the artery or vein and further are not suitable for arteries that are bent or curved or for long lesions; multiple stents are required. These designs do not provide any support to hold the wall of the artery, other than the memory of the metal.

Wall Stent, produced by Pfizer Inc., is a braided wire tube. Although this stent is flexible so as to be placed in curved arteries or veins and other body cavities, it does not have any radial strength imparted to it by design.

Wiktor, U.S. Pat. Nos. 4,649,922; 4,886,062; 4,969,458; and 5,133,732 describe a wire form stent. He describes stents made of wire helix made of a preformed wire which is in the sinusoidal form, in which either all or some of the adjacent strands are connected.

Arthus Fontaine, U.S. Pat. No. 5,370,683, also describes a similar device where a flat wire form of sinusoidal shape is wound on a mandrel to form a helical coil. the wire bends are "U" shaped and are connected to alternate "U"-shaped bands.

Allen Tower, U.S. Pat. Nos. 5,217,483 and 5,389,106 describes a similar device where the wire is preformed to a sinusoidal shape and subsequently wound on a mandrel to form a helical coil.

All of the above-described art fails to provide radial support. The preshaped wire form (sinusoidal in most of the prior art) is wrapped on a mandrel to form a coil. However, the forces imported by the vessel wall's hoop strength are radially inward. In other words, the force is acting perpendicular to the plane of the U-shaped wire form. This means that the bends that are in the wire add no structural strength to the wire form to support the force produced by the wall, which is radially inward.

When we examine the simple coils, such as taught in Scott U.S. Pat. No. 5,383,928 or Gene Samson U.S. Pat. No. 5,370,691 or Rolando Gills U.S. Pat. No. 5,222,969, it is apparent that the spring coil will withstand substantial radial forces due to the vessel wall; however, all these stents are bulky in their pre-expanded form and are hard to place in small and curved arteries or veins of the body. Also, a major disadvantage of this design is that when the coil stent is placed in a curved artery or vein, it forms an "accordion" shape whereby some strands in the outer radius are spread and those of the inner radius are gathered. Spring coils can also "flip" to form a flat structure when a longitudinal force is applied on one side of the stent.

The other types of stents that have been developed are tube stents. Palmer, U.S. Pat. Nos. 4,733,665; 4,739,762; 7,776,337; and 4,793,348 describe such a tube stent of slotted metal tube. The slotted metal tube is expanded by a high-pressure balloon to implant the stent into the inside wall of the artery or vein.

Joseph Weinstein, U.S. Pat. No. 5,213,561 describes a similar stent made of tubular materials with slots cut into it. On expansion using a balloon, it forms a structure with diamond-shaped slots.

Henry Wall, U.S. Pat. No. 5,266,073 also describes a stent, tubular, that has slots machined into it. When expanded, the edges of the stent lock to form a cylinder. Not only is this device stiff and can only be used for short lesions, but also the diameter cannot be adjusted to meet the exact needs of the particular vessel but it is fixed to the predetermined sizes.

Lau and Hastigan, U.S. Pat. No. 5,344,426 describes a slotted tubular stent that has a structure similar to Henry Wall's but has provided prongs that will lock in as the stent is expanded.

Michael Marin, U.S. Pat. No. 5,397,355 also describes a tubular slotted stent with locking prongs.

U.S. Pat. No. 5,443,500 illustrates the use of square openings with rectangular prongs that stick therethrough to lock the stent. This design, as well as other locking mechanisms, generally have resulted in very stiff stents because of the use of a tubular-type grid construction. Further, the locking devices have resulted in sharp outwardly oriented tabs which are used for the locking, which could cause vascular damage.

All the above-described tube stents, although typically providing substantial radial support when expanded, are not flexible enough to be placed in curved vessels. Arteries and veins in the human body are mostly curved and are tapered. As such, these tube stents suffer from this main disadvantage.

European patent document 042172982 employs wires that are doubled up and whose ends are snipped off to make a given joint. Such doubling up at the junction of two elements with snipped off free ends creates a potential puncture problem upon radial expansion. The sheer bulk of the doubled up wires makes them rotate radially outwardly away from the longitudinal centerline of the stent, while the plain ends on such an arrangement which are snipped off offer the potential of sharp points which can puncture or damage the intima. On the other hand, the apparatus of the present invention, employing sharp angles, as defined, avoids this problem in an embodiment which illustrates a continuous wire or wire-like member bent into a sharp angle. This type of structure alleviates the concerns of sharp edges, as well as the tendency of a doubled up heavy joint to rotate outwardly toward the intima upon radial expansion of the stem, as would be expected in the EPO reference 042172982.

Often these stents are layered with polymeric sheaths that are impregnated with biocompatible substances or can be coated with heparin or hydrogel. Most sheath-type coatings reduce endothelial cell growth through the stent, which is a major requirement in successful stenting of body cavities such as arteries and veins.

Several parameters in design of stents are important. Of the more important parameters is the issue of recoil. Recoil deals with the memory of the stent material which, generally speaking, upon expansion in the blood vessel will want to recoil back to its original shape. This can be problematic because it is desirable for the stent, once expanded, to remain in good contact with the vessel wall to avoid longitudinal shifting. Furthermore, any recoil constricts the flow passage and presents a greater portion of the stent in the blood flowpath, thus creating additional complications due to the turbulence which ensues.

Related to the concern regarding recoil is another concern regarding component twist. This phenomenon generally occurs when the cross-sectional area of the components is rectangular, such as when the stent is manufactured from a cylindrical piece which is then cut by lasers or other means to form the particular pattern. Particularly in the honey-combed designs involving the use of square or rectangular element cross-sections, radial expansion of such stents generally results in a twist of the component segments such that they extend into the flowpath in the artery or vein. Again, this causes turbulence which is undesirable.

Related to the problem of recoil or constriction after expansion is the ability of the stent to anchor itself in the vascular wall. An anchoring system that does not cause trauma is a desirable feature not found in the prior art.

Yet other considerations which are desirable in a stent not found in the prior art is the flexibility to be maneuvered around bends in the vascular system, coupled with the ability to conform to a bend without kinking or leaving large open areas. The stents of the present invention have the objective of addressing the issue of recoil, as well as providing an anchoring mechanism to fixate the stent once set. Several of the designs incorporate flexibility to allow the stent to follow a bend or curve in a vascular flowpath while a the same time providing sufficient radial deformation to ensure proper fixation while minimizing angular twisting movements of the stent components to minimize turbulence through the stent.

In a recent article appearing in late 1995, by Dr. Donald S. Baim, entitled "New Stent Designs," a description is given of the ideal endovascular prosthesis. There, Dr. Baim indicates that the ideal stent should have low implantation profile with enhanced flexibility to facilitate delivery. He goes on to say that the stent should be constructed from a noncorrosive, nonthrombogenic radiopaque alloy and have expanded geometry which maximizes radial strength to resist vascular recoil. The ideal stent described by Baim is further described as having a wide range of diameters and lengths. Dr. Baim concludes that it is unlikely that any current designs satisfy all these requirements. Thus, one of the objectives of the present invention is to go further than the prior designs in satisfying the criteria for the ideal designs as set forth by Dr. Baim in his recent article.

SUMMARY OF THE INVENTION

The invention discloses a stent which has a locking feature to prevent recoil. The stent is composed of a plurality of rings which are joined by crossties of various construction. The locking feature of each ring can be in alignment or staggered. The crossties may be straight or angled or they may have curvature to them to further promote longitudinal flexibility. The locking mechanism includes features which minimize sharp ends exposed to the vascular wall.

DETAILED DESCRIPTION OF THE PREFERRED EMBODIMENT

Figure 1:
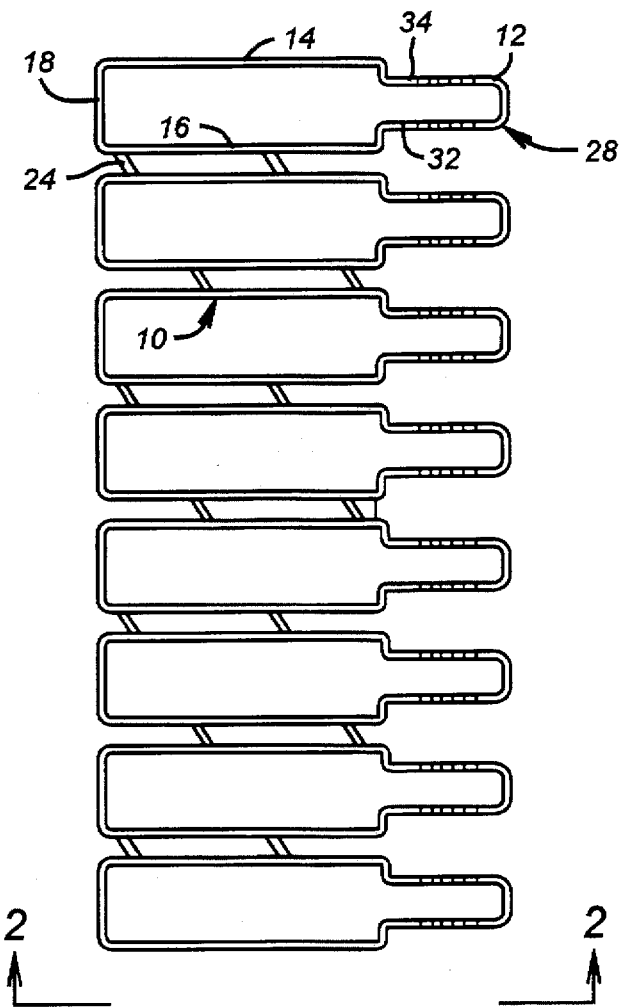
FIG. 1 is a flattened view of the plurality of rings which, when rolled into a cylinder, represent one version of the stent.
Figure 11:
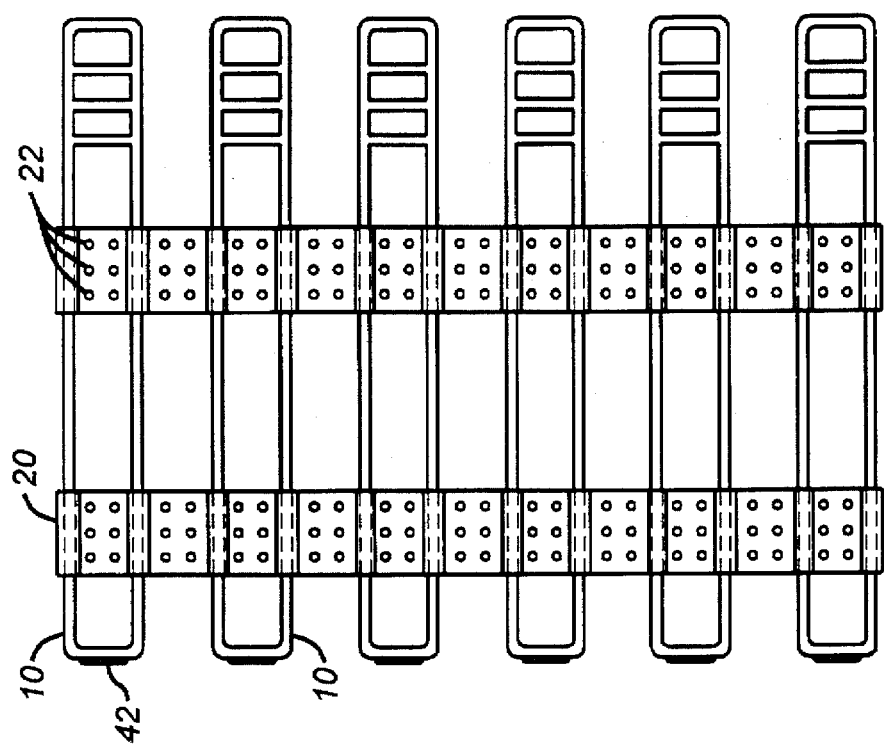
FIG. 11 uses broad crossties with the locking feature illustrated in FIG. 10.
Figure 10:
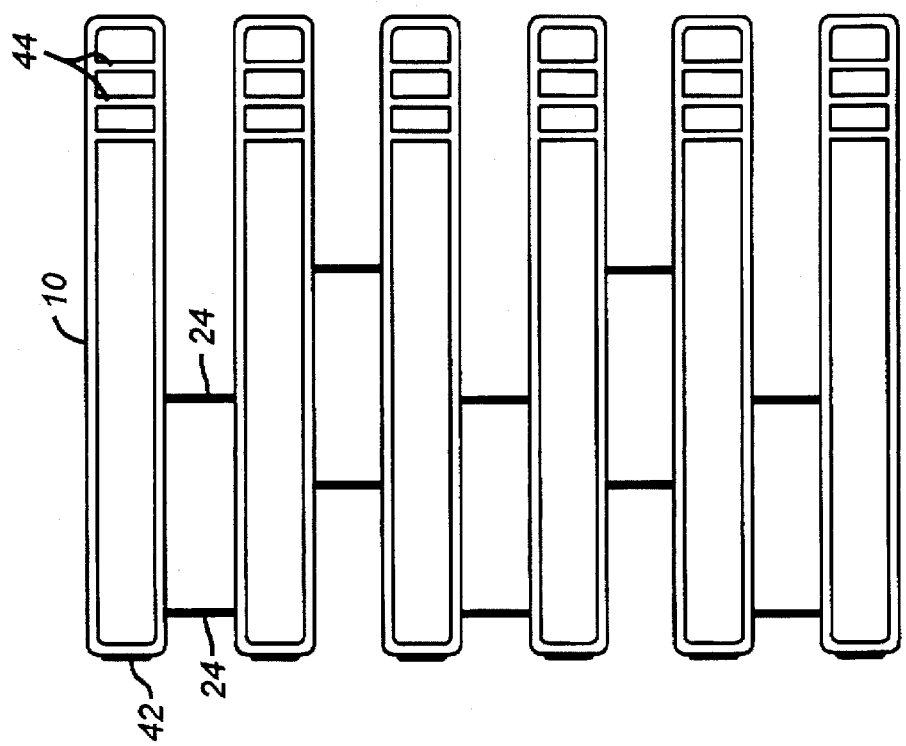
FIG. 10 is an alternative design of the locking feature, using staggered crossties.
Figure 13:
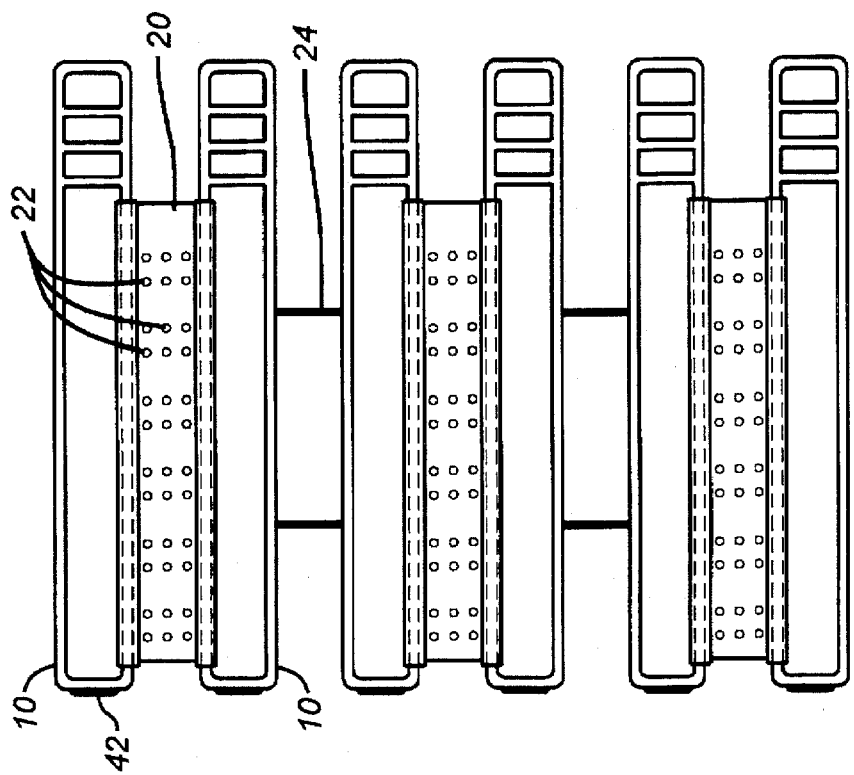
FIG. 13 shows an alternating design of broad crossties followed by narrow crossties, with the narrow crossties in alignment.
Figure 12:
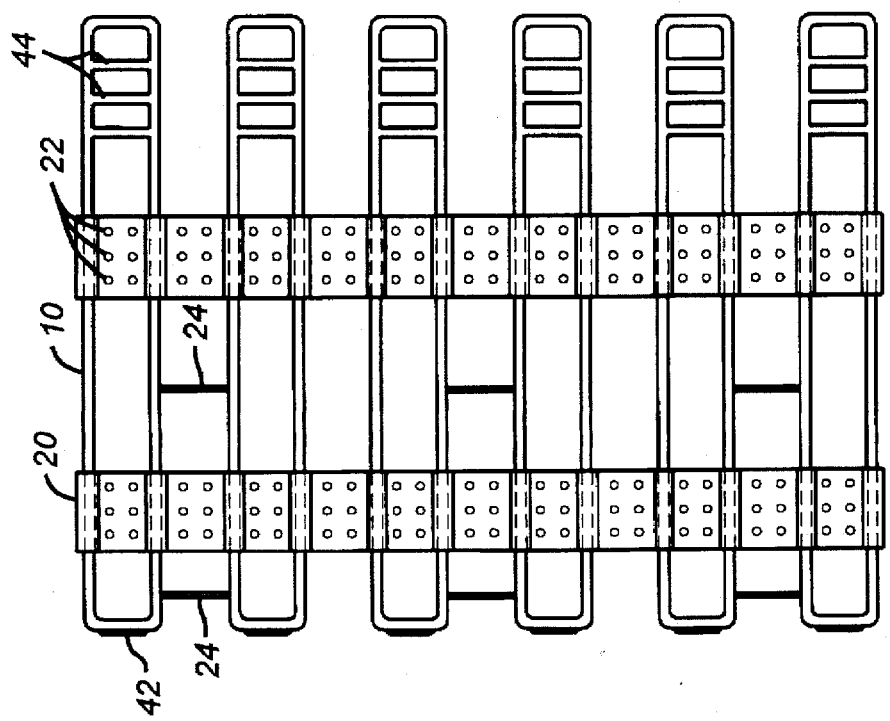
FIG. 12 is the stent of FIG. 11, using a combination of broad and narrow crossties, with the narrow crossties staggered.
Figure 14:
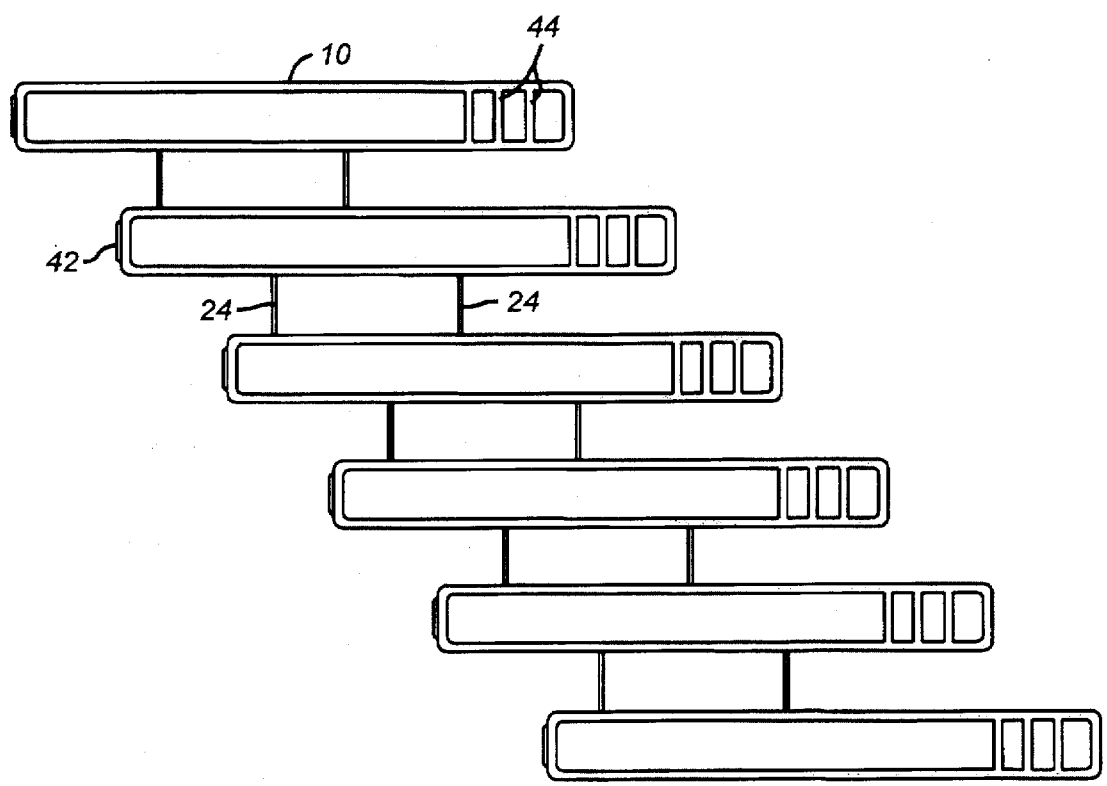
FIG. 14 is yet another variation using narrow and straight crossties that are misaligned, with the locking feature as illustrated in FIG. 10.
Figure 15:
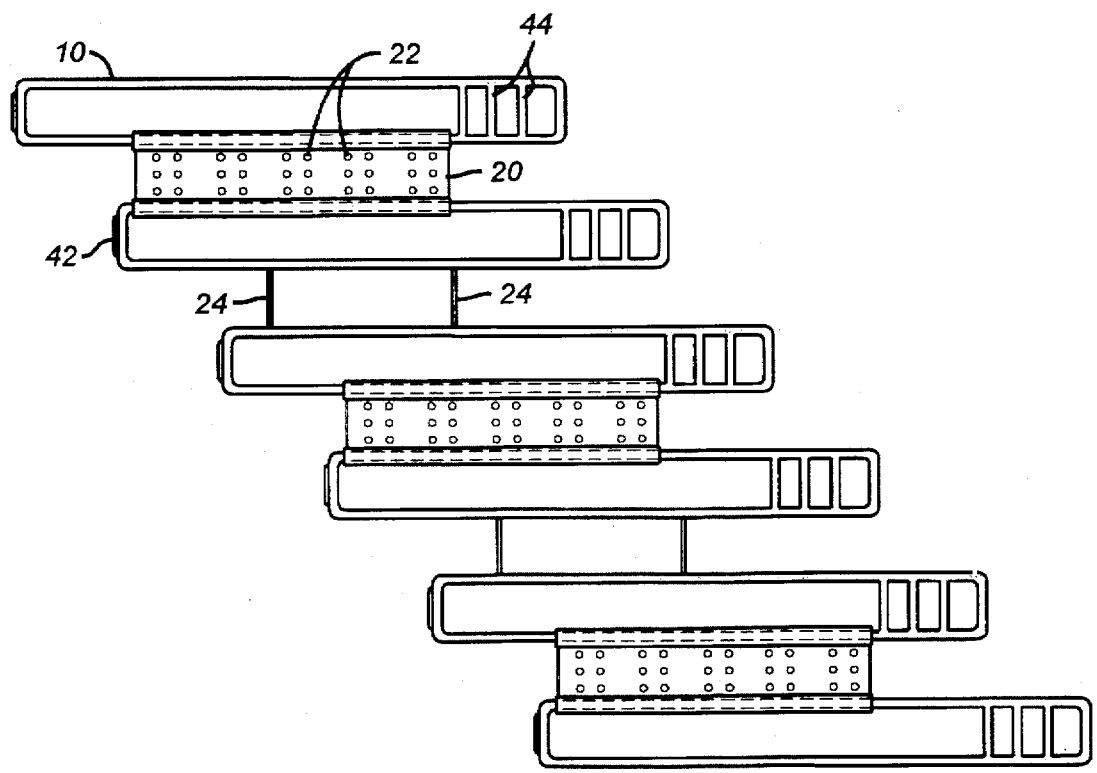
FIG. 15 illustrates the locking feature of FIG. 10 with an offset arrangement so the locking feature, when the stent is rolled, is misaligned from one ring to the next and using further crossties which represent alternating broad bands and narrow bands.

Referring now to FIG. 1, the stent is shown in an unrolled form prior to rolling it on a mandrel. The stent is made up of a plurality of component ring members 10. The rings can be made from stainless steel/titanium, copper/nickel, or nickel/titanium alloys, among others. The wire shape of ring members 10 can be formed of wire having various cross-sections such as round, rectangular or oval, to name a few. Each of the ring members 10 comprises a tab segment 12. In the view of FIG. 1, each ring member 10 has a pair of opposed segments 14 and 16 connected by a transverse segment 18. The tab segment 12 also connects the parallel segments 14 and 16 on the opposite end from transverse segment 18. The details of the transverse segment 18 and the tab segment 12 are more clearly illustrated in FIGS. 5–8 as well as FIG. 16. Between each ring member 10 are one or more crossties 20, 24 or 26. The crossties can be at any angle between the rings 10. While 45° is shown in FIG. 1, the angle can vary between 0°–90°. In FIG. 1, the crossties 24 are shown as thin, straight members. However, the crosstie arrangement can be offered in a number of different varieties. For example, the crossties 24 can be staggered as shown in FIG. 10. That is to say, between one ring 10 and the next, the crossties are not in longitudinal alignment. This gives the completed stent additional flexibility because it does not have a rigid spine which is created by the alignment of crossties. The crossties themselves may have some flexibility as illustrated by the wavy shape of the crossties 26 in FIG. 16. Here, the crossties 26 adopt a generally S-shape, giving them further additional flexibility to stretch longitudinally and transverse to the longitudinal axis, thus giving the stent formed by the design of FIG. 16, which is preferred, additional flexibility in flexing about its longitudinal axis. The crossties 20 can be a perforated banded material, as illustrated in FIGS. 11, 12, 13, or 15. The crossties can be made from stainless steel, plastics such as polyethylene, nylon, polyimide or polyester, etc. Here, the crossties 20, such as in FIG. 11, are in alignment from ring to ring but have a hinge-type or twisting flexibility as between one ring 10 and another. The ties 20 may be of a short width as shown in FIG. 11 or longer as shown in FIG. 13. The crossties 20 in FIG. 13 are of a unitary construction with a series of perforations 22. These types of crossties using the banding that is provided with perforations 22 can be used exclusively as shown in FIG. 11 or in conjunction with thin, straight crossties, such as 24 shown in FIG. 13. Alternatively, the flexible version of the crossties 20 shown in FIG. 16, which are wavy or S-shaped, can be used in lieu of the crossties 24, such as illustrated in FIG. 13. The embodiment of FIG. 14 illustrates the crossties 24 used exclusively without the wide banded crossties reflected in FIGS. 11–13. The crossties 20 in FIG. 15 are presented in an alternating pattern with crossties 24. Again, the crossties 26, shown in FIG. 16, can be interspersed with the crossties 20 illustrated in FIG. 15. In each case, the banded-type crossties 20 can be used in combination with crossties 24 or 26 and can be used in segmented form as shown in FIG. 12, where they cover substantially less than 90° of the stent that is produced from rolling such structures and locking them, or where substantially greater than 270° of the stent periphery is covered by the bands 20 (see FIG. 15).

Figure 5:
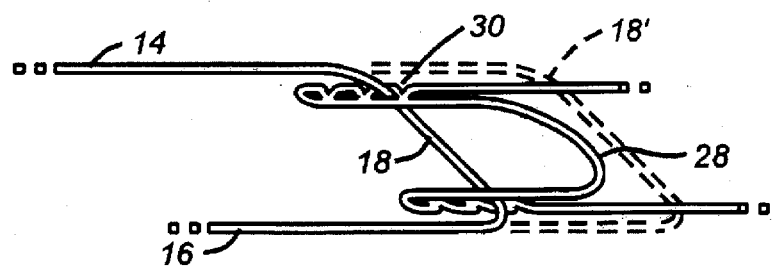
FIGS. 5–8 illustrate various techniques for locking the individual rings when rolled.

The operation of several different embodiments of the locking feature is illustrated in FIGS. 5–8. There, the tab segment 12 generally has a U-shaped end portion 28 and a series of undulations 30, any one of which is capable of trapping the transverse segment 18. It is clear to see by looking at FIGS. 1 and 5 in conjunction that the individual rings 10, when rolled around a mandrel, are preferably rolled to an initial diameter which places the transverse segment 18 in the position shown toward the dotted lines in FIG. 5. When a balloon catheter is placed at the desired location, the balloon can then be expanded, which expands the stent in a known manner, or alternatively the stent can be held compressed in a small-diameter state with various types of retention mechanisms, such as sleeves which keep it from expanding. When the desired location is reached, the stent can be expanded using a balloon or allowed to expand by removing any constraints against expansion. When this occurs, the transverse segment 18', shown in dashed lines in FIG. 5, begins to move toward the undulations 30. Eventually, the rings 10 are expanded sufficiently so that the transverse segment 18 jumps over at least one of the undulations 30. The undulations 30, as shown in FIG. 5, are slanted in such a manner so as to trap the transverse member 18. The operation is similar to a ratchet where advancement in one direction is possible but is blocked in the opposite direction. With this design, the undulations 30 provide the ratchet in combination with the U- or V-shaped segment 28 which is bent over backwards over the undulations 30, leaving a sufficient gap for the transverse member 18 to move in between. Upon expansion of the stent comprising of rings 10, the ratchet mechanism of the undulations 30 allows the expansion to continue as the transverse segment 18 jumps over the undulations 30. When the stent made up of rings 10 has been sufficiently expanded in the vascular system at the desired location, the expanded state is retained and recoil is thus eliminated using this ratchet-type undulation system.

Figure 6:
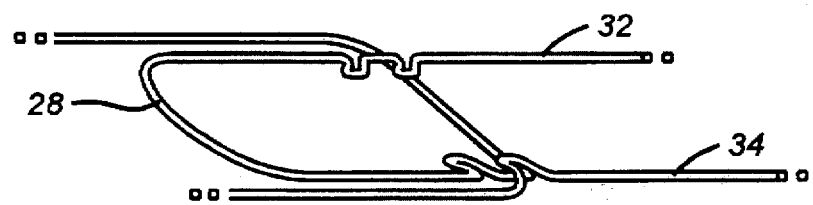

The differences between the embodiment in FIGS. 5 and 6 are readily apparent from examining the drawings. The basic difference is that the U-shaped segment 28, rather than being bent over the undulations 30, is itself in the same plane, prior too rolling, as segments 32 and 34, which comprise the tab portion 12 as shown in FIG. 1.

Figure 7:
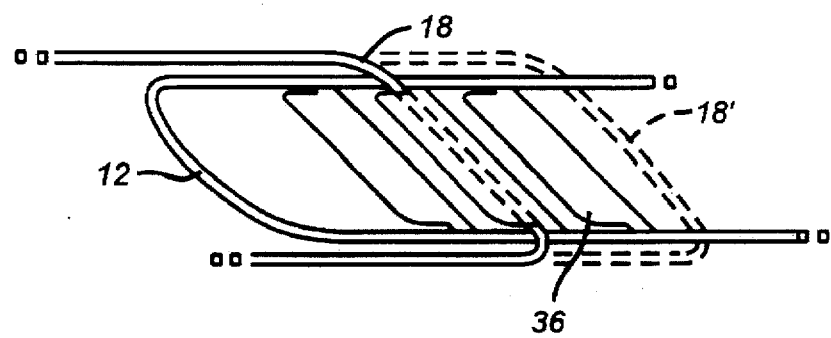

In a variation of the undulation ratchet-type locking mechanism shown in FIGS. 5 and 6, FIG. 7 illustrates a plurality of bent tabs 36 which are bent downwardly and oriented into the inside of the stent, rather than towards the wall of the artery. Once again, the initial position of the transverse member 18' is illustrated in FIG. 7 in dotted lines. As the stent expands or is expanded, the transverse member 18', which is literally below the tab portion 12, rides over the tabs 36. When the stent is fully expanded or been allowed to fully expand, the transverse member or segment 18 has skipped over at least one of the tabs 36 and, therefore, cannot collapse inwardly. The locking feature is thus illustrated which, again, is for the purpose of preventing recoil.

Figure 8:
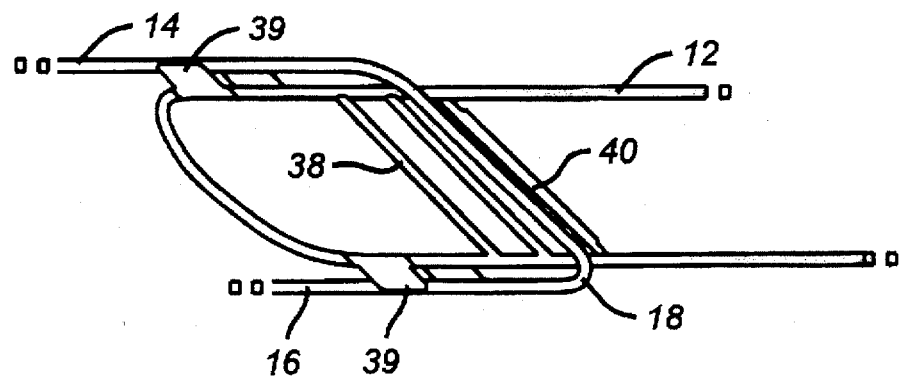
Figure 8A:
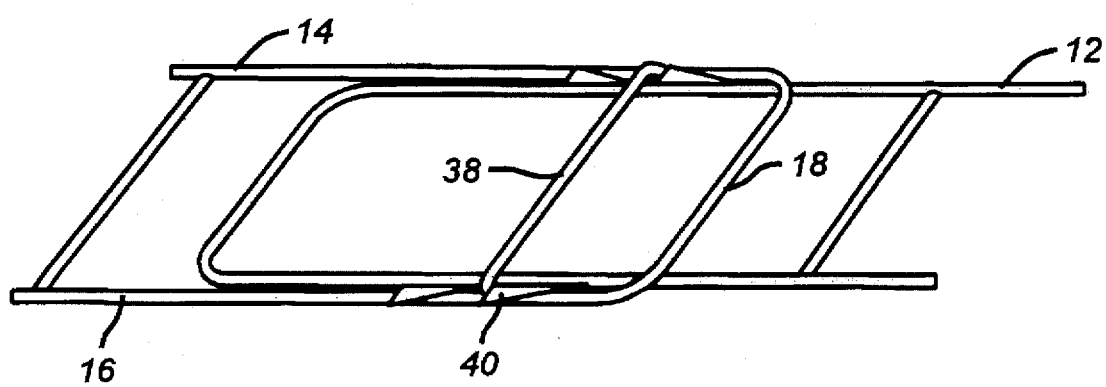
FIG. 8a is similar to FIG. 8 with the locking feature extending in a different direction than FIG. 8.

FIGS. 8 and 8a illustrate yet other embodiments of the locking feature. This time the tab portion 12 has a series of rungs 38, while the transverse segment 18 has an inwardly oriented tab 40. This time the transverse segment 18 rides over the tab 40 so that the ratchet function is again achieved when the inwardly (FIG. 8) or laterally (FIG. 8a) oriented tab 40 jumps over the rungs 38 and traps itself between any two of such rungs 38. The segments 14 and 16, which in this embodiment overlay the tab 12, hold down to tab 12 by a series of tabs 39, which are secured to segments 14 and 16 and help the tab portion 12 slide over segments 14 and 16.

Figure 2:
FIG. 2 is a view seen along lines 2—2 of FIG. 1.
Figure 3:
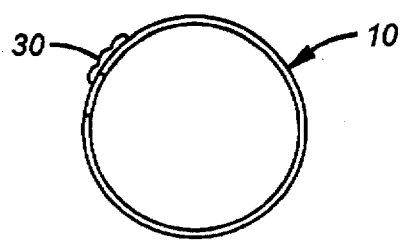
FIG. 3 is the view of FIG. 2, after rolling the flattened stent into a cylindrical shape.
Figure 4:
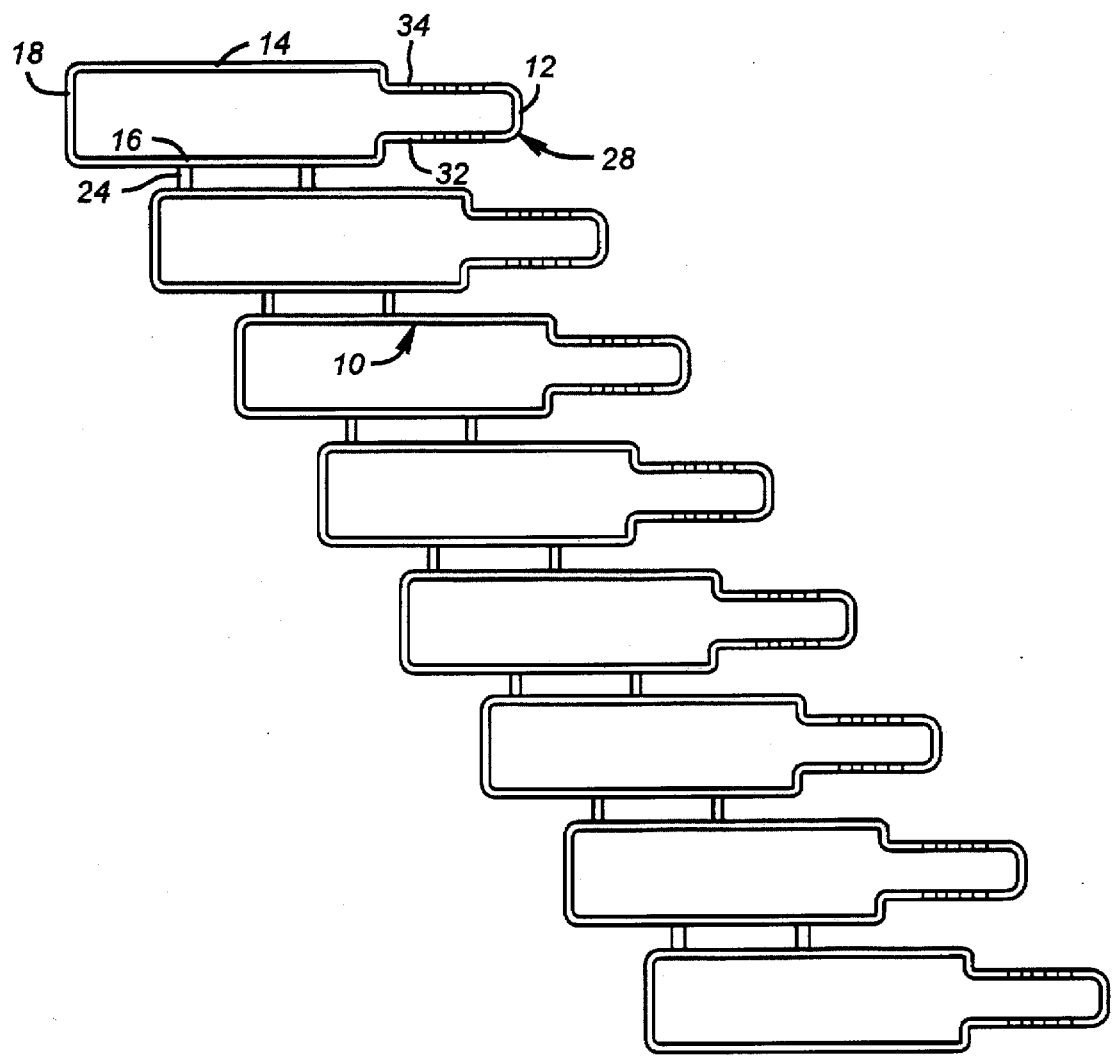
FIG. 4 is an alternative embodiment of FIG. 1 and illustrates the use of staggered locking mechanisms such that when rolled, the locking mechanisms are not in alignment.
Figure 9:
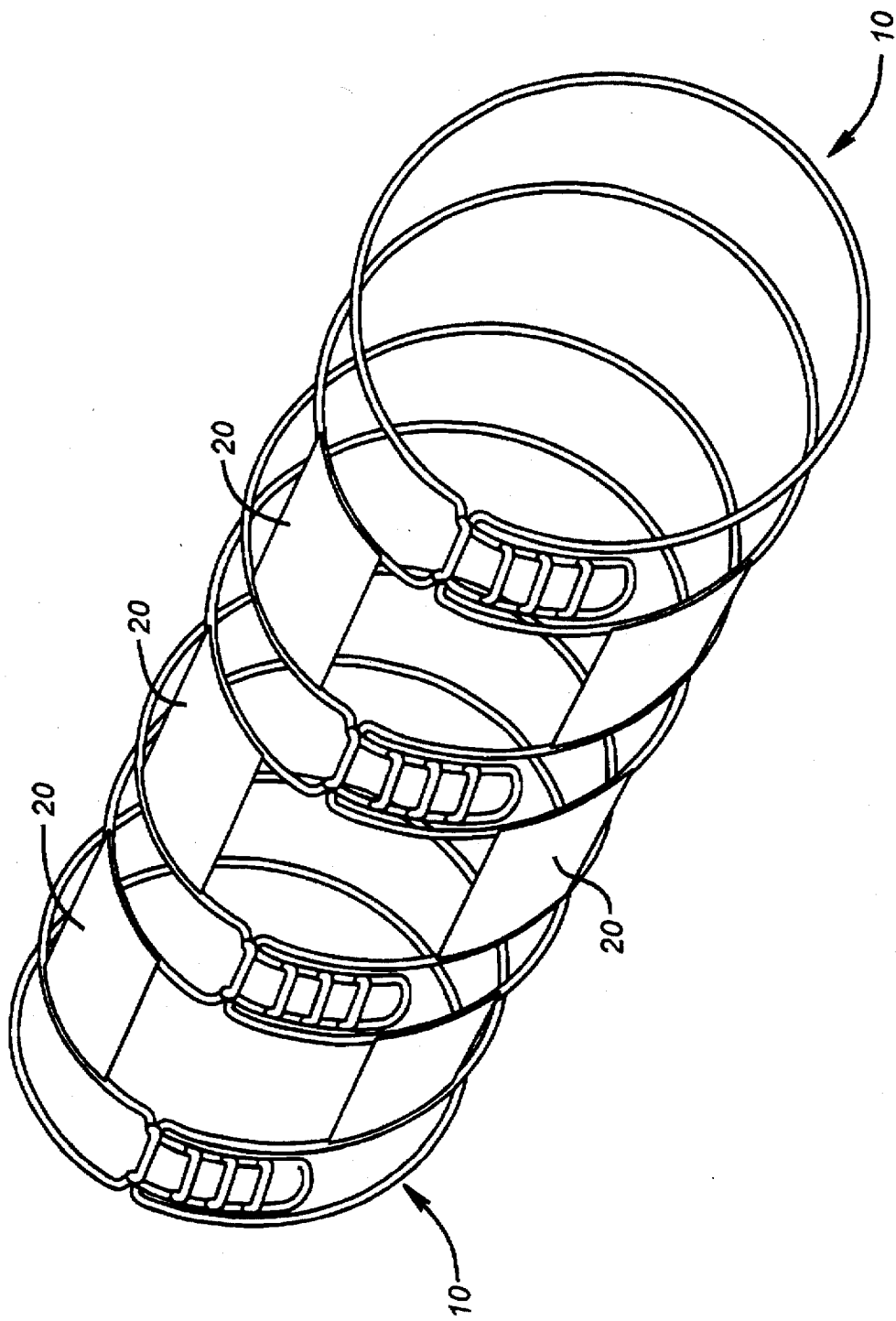
FIG. 9 is a perspective view of the stent, showing broad members as the crossties, with the locking features in alignment as well as the crossties in alignment.

FIG. 9 shows in perspective the ring assembly, using the rings 10 with crossties 20 which are of the segmented band type shown in longitudinal alignment. Again, the wide varieties of different crosstie arrangements shown in FIGS. 10–16 could also be employed in the design shown in FIG. 9. FIG. 3 illustrates a single ring 10, which is illustrated in FIG. 1 after it is rolled around a mandrel and secured, using the locking technique of the undulations 30, such as shown in FIG. 5. FIG. 2 simply gives a side view of the plurality of rings when still arranged flat prior to rolling them around a mandrel. The ring 10 is illustrated with the undulations 30, followed by the U-shaped segment 28.

As shown in FIGS. 10–15, different arrangements of crossties 20–26 are illustrated. The locking arrangement consists of an inwardly oriented tab 42 and a ladder arrangement consisting of rungs 44 at the opposite end of each of the ring segments 10. It can be appreciated that the design of FIGS. 11 and 12 are somewhat stiffer since the individual rings cannot easily translate parallel to each other in view of the design of the crossties 20. In the design of FIG. 10, there is more flexibility than the design of FIGS. 11 and 12 in that the crossties 24 have some limited amount of give. It is clear that the design of FIG. 16 has the most longitudinal flexibility in that the locking mechanisms L are offset from each other and the crossties 26 have transverse and longitudinal flexibility due to their wavy or S-shape.

Figure 16:
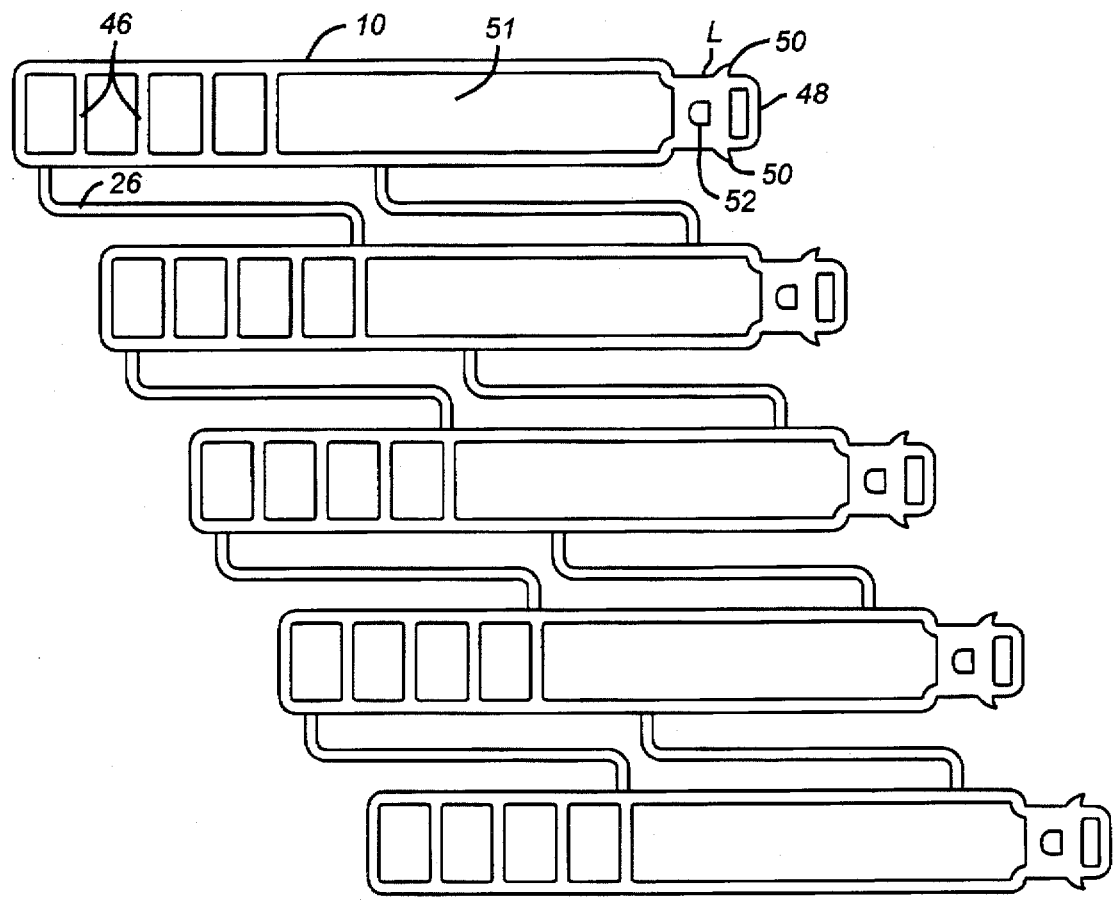
FIGS. 16 and 16A illustrates the use of flexible crossties and yet another variation of the locking feature.
Figure 16A:
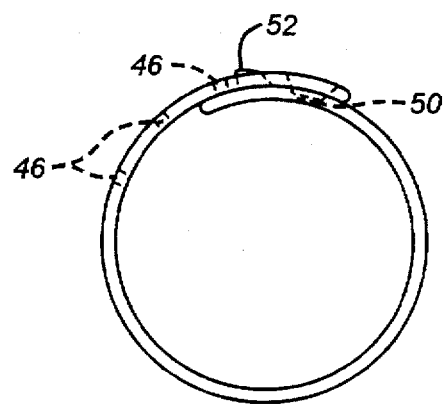

Referring now specifically to the design of FIG. 16, the rings are as previously described in FIG. 1. Rings 10 have a plurality of rungs 46, while a tab 48 (shown in FIG. 16 in flattened form) and illustrated in FIG. 16A to have guides 50 oriented inwardly into opening 51 when the rings 10 are rolled to make the stent in a compressed state. As the stent expands, or is expanded, the guides 50 ride in opening 51 until the inwardly oriented projections 50, shown in FIG. 16A, ride in opening 51 and then over the rungs 46, which allows the rings 10 to expand and to lock the expanded position as the tab 52 traps one of the rungs 46 (see dashed lines in FIG. 16A). The operation is akin to a ratchet in this design, the lock mechanisms L are circumferentially offset from one ring 10 to another. Each of the rings 10 has flexibility to move parallel to the adjacent ring 10 due to the design of the crossties 26. Each ring 10 also has the flexibility to move closer to or away from its adjacent ring 10, again giving this stent design additional flexibility, both longitudinally and in a transverse plane to the longitudinal axis.

The designs in FIGS. 10–15 illustrate a similar type of locking mechanism using the ladder with inwardly oriented tab approach, either aligning the locking mechanisms L or offsetting them as shown in FIGS. 14 and 15. Different combinations of crossties are illustrated, using crossties 20 or 24. Crossties 20 can be individually less than 180°, or if a single band is used, it is preferably more than 270°. The crossties 24 when used are represented in longitudinally aligned format, such as in FIG. 13, or in misaligned formats, such as FIGS. 10 and 14. The crosstie designs can be mixed or matched as illustrated in FIGS. 10–16A. As shown in FIG. 15, the offsetting of the crossties, whether type 20 or 24 are illustrated, gives the stent longitudinal flexibility to move through a tortuous path and to adapt to that shape. Depending on the application, different combinations of crossties can be employed, and different placements of the locking mechanism L can be used to obtain greater or lesser degrees of rigidity in the stent. When using the band-type crosstie 20, the openings 22 provide needed circulations to the cells in the vascular wall to prevent damage thereto. The locking mechanism L as illustrated in the various permutations avoids the use of singular sharp ends of wires or flaps outwardly pointing which could cause vascular damage. In a departure from prior stent designs, the locking mechanism L, which is illustrated in the figures, accomplishes the locking objectives without sharp ends oriented toward the vascular wall. Locking mechanisms that operate sideways rather than radially inward do not depart from the spirit of the invention. The locking mechanisms have also been staggered to provide additional flexibility as compared to a design where all the locks are aligned, which tends to be stiffer than offsetting them. By providing designs of crossties such that will allow additional flexibility between the ring members 10, the assembled stent is more amenable to adopt a tortuous shape in the passages where it will be set. Any of the crossties illustrated can be made of a radiopaque material to facilitate the installation of the stent and subsequent diagnoses.

The use of crossties, whether staggered or aligned, presents an improvement over prior designs which use the grid system. The grid system resulted in extremely stiff stents which were difficult to place in tortuous portions of the vascular system.

Various biocompatible materials can be used to make the rings 10 and the locking components L thereof. The invention encompasses stents which are delivered by balloon catheters or by other means which retain the assembled stent in a compressed condition, only to allow it to spring outwardly when placed at the desired location.

The foregoing disclosure and description of the invention are illustrative and explanatory thereof, and various changes in the size, shape and materials, as well as in the details of the illustrated construction, may be made without departing from the spirit of the invention.

I claim:

1. A stent, comprising:
   a plurality of spaced-apart components having opposed ends, said components capable of being rolled into a tubular shape, by overlapping one end on said other end on said plurality of components without any one end passing through its respective component and further comprising a locking assembly which allows said rolled components to expand to at least one predetermined dimension and to lock such position against recoil by locking overlapping ends;
   at least one crosstie connecting said components.

2. The stent of claim 1, wherein said locking assembly further comprises a ratchet-type mechanism formed by overlapping ends of said plurality of rolled components.

3. The stent of claim 1, wherein said crosstie flexibly connects said components to allow relative movement therebetween in a plurality of directions.

4. The stent of claim 1, wherein said crosstie comprises a thin elongated member.

5. A stent, comprising:
   a plurality of spaced-apart components capable of being rolled into a tubular shape, said plurality of components comprising a locking assembly which allows said rolled components to expand to at least one predetermined dimension and to lock such position against recoil by locking overlapping portions of said plurality of components;
   at least one crosstie connecting said components;
   said crosstie comprises a thin elongated member; and
   said crosstie comprises at least one bend.

6. The stent claim 5, comprising:
   a plurality of spaced-apart components capable of being rolled into a tubular shape, said plurality of components comprising a locking assembly which allows said rolled components to expand to at least one predetermined dimension and to lock such position against recoil by locking overlapping portions of said plurality of components;
   at least one crosstie connecting said components; and
   said crosstie comprises a perforated band.

7. The stent of claim 6, wherein said band extends to less than 90° circumferentially and a plurality of such bands between adjacent components are used.

8. The stent of claim 6, wherein said crosstie comprises a single band covering at least 270° circumferentially between adjacent components.

9. A stent comprising:
   a plurality of spaced-apart components capable of being rolled into a tubular shape, said plurality of components comprising a locking assembly which allows said rolled components to expand to at least one predetermined dimension and to lock such position against recoil by locking overlapping portions of said plurality of components;
   at least one crosstie connecting said components;
   said components comprise an enclosed wire shape having at least one transverse segment separating two substantially parallel segments and a tab portion opposite said transverse segment to complete said enclosed shape; and
   said tab comprising an undulation which, upon expansion of each said shape, brings said transverse member in locking engagement with at least one said undulation.

10. A stent comprising:
    a plurality of spaced-apart components capable of being rolled into a tubular shape, said plurality of components comprising a locking assembly which allows said rolled components to expand to at least one predetermined dimension and to lock such position against recoil by locking overlapping portions of said plurality of components;

at least one crosstie connecting said components;

said components comprise an enclosed wire shape having at least one transverse segment separating two substantially parallel segments and a tab portion opposite said transverse segment to complete said enclosed shape;

said tab comprises at least one rung; and said transverse segment comprises an extending member oriented inwardly or laterally with respect to said rolled up shape which upon expansion of said shape engages said rung.

11. A stent comprising:

a plurality of spaced-apart components capable of being rolled into a tubular shape, said plurality of components comprising a locking assembly which allows said rolled components to expand to at least one predetermined dimension and to lock such position against recoil by locking overlapping portions of said plurality of components;

at least one crosstie connecting said components;

said components comprise an enclosed wire shape having at least one transverse segment separating two substantially parallel segments and a tab portion opposite said transverse segment to complete said enclosed shape;

said tab comprises at least one rung with an inwardly or laterally extending member when said shape is rolled; and said transverse member, upon expansion of said shape, engaging said extending member to prevent recoil.

12. A stent comprising:

a plurality of spaced-apart components capable of being rolled into a tubular shape, said plurality of components comprising a locking assembly which allows said rolled components to expand to at least one predetermined dimension and to lock such position against recoil by locking overlapping portions of said plurality of components;

at least one crosstie connecting said components; and said locking assembly on one of said components is circumferentially offset from another of said components.

13. A stent comprising:

at least three spaced-apart components capable of being rolled into a tubular shape, said at least three components comprising a locking assembly which allows said rolled components to expand to at least one predetermined dimension and to lock such position against recoil by locking overlapping portions of said at least three components;

at least one crosstie connecting said components;

a plurality of crossties between said at least three components; and said crossties being aligned as between adjacent pairs of components.

14. A stent comprising:

at least three spaced-apart components capable of being rolled into a tubular shape, said at least three components comprising a locking assembly which allows said rolled components to expand to at least one predetermined dimension and to lock such position against recoil by locking overlapping portions of said at least three components;

at least one crosstie connecting said components;

a plurality of crossties between said at least three components; and said crossties being misaligned as between adjacent pairs of components.

15. A stent comprising:

at least three spaced-apart components capable of being rolled into a tubular shape, said at least three components comprising a locking assembly which allows said rolled components to expand to at least one predetermined dimension and to lock such position against recoil by locking overlapping portions of said at least three components;

at least one crosstie connecting said components;

a plurality of crossties between said at least three components; and said crossties are of different degrees of stiffness between any pair of components.

16. A stent comprising:

at least three spaced-apart components capable of being rolled into a tubular shape, said at least three components comprising a locking assembly which allows said rolled components to expand to at least one predetermined dimension and to lock such position against recoil by locking overlapping portions of said at least three components;

at least one crosstie connecting said components;

a plurality of crossties between said at least three components; and each of said crossties flexibly connects pairs of said components to allow relative movement in a plurality of directions.

17. The stent of claim 16, wherein each said crosstie comprises a thin, elongated member with at least one bend.

18. A stent comprising:

a plurality of spaced-apart components capable of being rolled into a tubular shape, said plurality of components comprising a locking assembly which allows said rolled components to expand to at least one predetermined dimension and to lock such position against recoil by locking overlapping portions of said plurality of components;

at least one crosstie connecting said components;

said components comprise an enclosed wire shape having at least one transverse segment separating two substantially parallel segments and a tab portion opposite said transverse segment to complete said enclosed shape; and wherein said tab portion comprises at least one guide member extending into the space between said two substantially parallel members to act as a guide until a catch member, extending inwardly or laterally from said tab when said shape is rolled, rides over said transverse segment to lock said shape against recoil.

19. The stent of claim 18, further comprising:

at least three components;

a plurality of crossties between said at least three components;

each of said crossties flexibly connects said components to allow relative movement in a plurality of directions.

20. The stent of claim 19, wherein each said crosstie comprises a thin, elongated member with at least one bend.

21. A stent comprising:

a plurality of spaced-apart components capable of being rolled into a tubular shape, said plurality of components comprising a locking assembly which allows said rolled components to expand to at least one predetermined dimension and to lock such position against recoil by locking overlapping portions of said plurality of components;

at least one crosstie connecting said components;

said locking assembly further comprises a ratchet-type mechanism formed by overlapping ends of said plurality of rolled components; and said crosstie flexibly connects said components to allow relative movement therebetween in a plurality of directions.

22. The stent of claim 21, wherein said crosstie comprises a thin elongated member.

23. The stent of claim 22, wherein said crosstie comprises at least one bend.

24. The stent of claim 23, wherein:

said components comprise an enclosed wire shape having at least one transverse segment separating two substantially parallel segments and a tab portion opposite said transverse segment to complete said enclosed shape;

said tab comprising an undulation which, upon expansion of each said shape, brings said transverse member in locking engagement with at least one said undulation.

25. The stent of claim 23, wherein:

said components comprise an enclosed wire shape having at least one transverse segment separating two substantially parallel segments and a tab portion opposite said transverse segment to complete said enclosed shape;

said tab comprises at least one rung;

said transverse segment comprises an extending member oriented inwardly or laterally with respect to said rolled up shape which upon expansion of said shape engages said rung.

26. The stent of claim 25, further comprising:

at least three components;

a plurality of crossties between said at least three components.

27. The stent of claim 26, further comprising:

said plurality of crossties being aligned as between adjacent pairs of components.

28. The stent of claim 26, further comprising:

said plurality of crossties being misaligned as between adjacent pairs of components.

29. The stent of claim 26, further comprising:

said plurality of crossties are of different degrees of stiffness between any pair of components.

30. The stent of claim 26, further comprising:

said plurality of crossties flexibly connect pairs of said components to allow relative movement in a plurality of directions.

31. The stent of claim 30, wherein said plurality of crossties comprise a thin, elongated member with at least one bend.

32. The stent of claim 25, wherein:

said component comprises an enclosed wire shape having at least one transverse segment separating two substantially parallel segments and a tab portion opposite said transverse segment to complete said enclosed shape;

wherein said tab portion comprises at least one guide member extending into the space between said two substantially parallel members to act as a guide until a catch member, extending inwardly or laterally from said tab when said shape is rolled, rides over said transverse segment to lock said shape against recoil.

33. The stent of claim 23, wherein:

said components comprise an enclosed wire shape having at least one transverse segment separating two substantially parallel segments and a tab portion opposite said transverse segment to complete said enclosed shape;

said tab comprises at least one rung with an inwardly or laterally extending member when said shape is rolled;

said transverse member, upon expansion of said shape, engaging said extending member to prevent recoil.

34. The stent of claim 23, wherein said locking assembly on one of said components is circumferentially offset from another of said components.

* * * * *